US007018654B2

(12) United States Patent
Kirk et al.

(10) Patent No.: US 7,018,654 B2
(45) Date of Patent: Mar. 28, 2006

(54) PHARMACEUTICAL COMPOSITION CONTAINING AN ACTIVE AGENT IN AN AMINO ACID COPOLYMER STRUCTURE

(75) Inventors: Randal J. Kirk, Radford, VA (US); Keith R. Latham, Abingdon, VA (US)

(73) Assignee: New River Pharmaceuticals Inc., Radford, VA (US)

( * ) Notice: Subject to any disclaimer, the term of this patent is extended or adjusted under 35 U.S.C. 154(b) by 390 days.

(21) Appl. No.: 09/986,426

(22) Filed: Nov. 8, 2001

(65) Prior Publication Data

US 2002/0128177 A1 Sep. 12, 2002

Related U.S. Application Data

(63) Continuation-in-part of application No. 09/959,396, filed as application No. PCT/US00/05693 on Mar. 6, 2000, now abandoned, and a continuation-in-part of application No. 09/411,238, filed on Oct. 4, 1999, now abandoned, which is a continuation-in-part of application No. 09/265,415, filed on Mar. 10, 1999, now abandoned.

(60) Provisional application No. 60/123,146, filed on Mar. 5, 1999.

(51) Int. Cl.
*A61K 9/14* (2006.01)
*A61K 38/00* (2006.01)
*A61K 47/00* (2006.01)

(52) U.S. Cl. .......................... 424/484; 424/486; 514/2; 514/773

(58) Field of Classification Search ................ 424/484, 424/486, 78.08, 1.69, 9.34; 514/2, 773; 435/174
See application file for complete search history.

(56) References Cited

U.S. PATENT DOCUMENTS

| | | |
|---|---|---|
| 3,331,814 A | 7/1967 | Randall .......................... 26/78 |
| 3,846,399 A | 11/1974 | Hirschmann et al. |
| 3,975,342 A | 8/1976 | Gross |
| 4,040,907 A | 8/1977 | Ullman et al. |
| 4,356,166 A | 10/1982 | Peterson et al. |
| 4,399,121 A | 8/1983 | Albarella et al. |
| 4,483,807 A | 11/1984 | Asano ........................ 264/22 |
| 4,552,864 A | 11/1985 | Antoni et al. |
| 4,569,844 A | 2/1986 | Jones ........................... 426/2 |
| 4,657,873 A | 4/1987 | Gadow ...................... 436/532 |
| 4,753,804 A | 6/1988 | Iaccheri ..................... 424/491 |
| 4,863,735 A | 9/1989 | Kohn et al. |
| 4,925,673 A | 5/1990 | Steiner ...................... 424/455 |
| 4,960,790 A | 10/1990 | Stella et al. |
| 4,976,962 A | 12/1990 | Bichon et al. |
| 5,057,317 A | 10/1991 | Iida ............................. 724/423 |
| 5,073,641 A | 12/1991 | Bundgaard et al. |
| 5,087,616 A | 2/1992 | Myers et al. |
| 5,169,933 A | 12/1992 | Anderson et al. |
| 5,219,564 A | 6/1993 | Zalipsky et al. |
| 5,234,696 A | 8/1993 | Van Scoik ................. 424/489 |
| 5,238,714 A | 8/1993 | Wallace et al. |
| 5,362,831 A | 11/1994 | Mongelli et al. |
| 5,451,410 A | 9/1995 | Milstein ..................... 424/496 |
| 5,534,496 A | 7/1996 | Lee et al. |
| 5,643,957 A | 7/1997 | Leone-Bay ................. 514/563 |
| 5,681,748 A | 10/1997 | DiSorbo ..................... 435/404 |
| 5,741,705 A | 4/1998 | Blom ......................... 435/348 |
| 5,756,291 A | 5/1998 | Griffin ........................... 435/6 |
| 5,762,909 A | 6/1998 | Uzgiris |
| 5,767,227 A | 6/1998 | Latham et al. |
| 5,776,885 A | 7/1998 | Orsolini ......................... 514/2 |
| 5,792,451 A | 8/1998 | Sarubbi ..................... 424/85.4 |
| 5,820,881 A | 10/1998 | Milstein ..................... 424/489 |
| 5,846,743 A | 12/1998 | Janmey et al. |
| 5,851,536 A | 12/1998 | Yager et al. |
| 5,861,387 A | 1/1999 | Labrie ........................ 514/169 |
| 5,882,645 A | 3/1999 | Toth et al. |
| 5,891,478 A | 4/1999 | Johnson ..................... 424/502 |
| 5,898,033 A | 4/1999 | Swadesh et al. |
| 5,910,569 A | 6/1999 | Latham et al. |
| 5,948,750 A | 9/1999 | Garsky et al. |
| 5,952,294 A | 9/1999 | Lazo et al. |
| 5,977,163 A | 11/1999 | Li et al. |
| 6,005,004 A | 12/1999 | Katz et al. |
| 6,030,941 A | 2/2000 | Summerton et al. |
| 6,306,993 B1 | 10/2001 | Rothbard et al. |
| 6,458,842 B1 | 10/2002 | Dickinson et al. |

FOREIGN PATENT DOCUMENTS

| | | |
|---|---|---|
| EP | 0 187 547 A2 | 7/1986 |
| FR | 2 533 222 | 3/1984 |
| JP | 52100486 | 8/1977 |
| JP | 55145736 | 11/1980 |
| JP | 04126160 | 4/1992 |
| WO | WO 95/12605 | 5/1995 |
| WO | WO 95/14033 | 5/1995 |
| WO | WO 97/36616 | 10/1997 |

OTHER PUBLICATIONS

Orten, James M. et al., "Thyroxine," *Human Biochemistry*, 9th Ed., C.V. Mosby Company, St. Louis, pp. 401–405 (1975).

(Continued)

*Primary Examiner*—David M. Naff
*Assistant Examiner*—Deborah K. Ware
(74) *Attorney, Agent, or Firm*—Hunton & Williams LLP

(57) ABSTRACT

A method of protecting a chemical compound from degradation comprising combining the chemical compound with an amino acid polymer. Disclosed are methods of combining chemical compounds with synthetic amino acid polymers for protection from degradation of the chemical compounds and to provide for controlled release of the compounds. A method is described for the selective release of drug substances from a synthetic amino acid polymer in the stomach or small intestine, utilizing pH-dependent changes in a higher order structure. A pharmaceutical composition comprising a drug substance that has been combined with an amino acid polymer and a pharmaceutically acceptable combination of excipients is disclosed. A cell culture media comprising a polypeptide containing glutamine that has been co-polymerized with an amino acid is described.

26 Claims, No Drawings

OTHER PUBLICATIONS

Li, Chun, et al., "Complete Regression of Well–Established Tumors Using a Novel Water–Soluble Poly(L–Glutamic Acid)–Paclitaxel Conjugate," *Cancer Res*, 58:2404–2409 (1998).

Kramer, Werner et al., "Intestinal Absorption of Peptides by Coupling to Bile Acids," *The Journal of Biochemistry*, 269(14):10621–10627 (1994).

Rawitch, Allen B., et al., "The Isolation of Identical Thyroxine Containing Amino Acid Sequences from Bovine, Ovine and Porcine Thyroglobulins," *Biochemical and Biophysical Research Communications*, 118(2):423–429 (1984).

Marriq, Claudine, et al., "Amino Acid Sequence of the Unique 3,5,3'–Triodothyronine–Containing Sequence from Porcine Thyroglobulin," *Biochemical and Biophysical Research Communications*, 112(1):206–213 (1983).

Sawada, Kyoko, et al., "Recognition of L–Amino Acid Ester Compounds by Rat Peptide Transporters PEPT1 and PEPT2," *Journal of Pharmacology and Experimental Therapeutics*, 291(2):705–709 (1999).

De Vrueh, Remco L.A., et al, "Transport of L–Valine–Acyclovir Via the Oligopeptide Transporter in the Human Intestinal Cell Line, Caco–2," *Journal of Pharmacology and Experimental Therapeutics*, 286(2):1166–1170 (1988).

Guo, Ailan, et al., "Interactions of a Nonpeptide Drug, Valacyclovir, with the Human Intestinal Peptide Transporter (hPEPT1) Expressed in a Mammalian Cell Line," *Journal of Pharmacology and Experimental Therapeutics*, 289(1):448–454 (1999).

Burnette, Thimysta C., et al., "Metabolic Disposition of the Acyclovir Prodrug Valaciclovir in the Rat," *Drug Metabolism and Disposition*, 22(1):60–64 (1994).

Aggarwal, et al., "Synthesis and Biological Evaluation of Prodrugs of Zidovudine," *J. Med. Chem*., 33(5):1505–1511 (1990).

Zunino, Franco, et al., "Comparison of Antitumor Effects of Daunorubicin Covalently Linked to Poly–L–Amino Acid Carriers," *European Journal of Cancer & Clinical Oncology*, 20(3):121–125 (1984).

Havranova, Marie et al., "A High–Molecular Mass Derivative of Trypsin–Kallikrein Inhibitor for Potential Medical Use, II," *Hoppe–Seyler's Z. Physiol. Chem*., 363:295–303 (1982).

Ryser, Hugues J.P., et al., "Conjugation of Methotrexate to Poly (L–lysine) increases Drug Transport and Overcomes Drug Resistance in Cultured Cells," *Proc. Natl. Acad. Sci. USA*, 75(8):3867–3870 (1978).

Han, Hyo–Kyung, et al., "Targeted Prodrug Design to Optimize Drug Delivery," *AAPS PharmSci*, 2(1): Article 6 (2000).

Tamai, I., et al., "Improvement of L–dopa Absorption by Dipeptidyl Derivation, Utilizing Peptide Transporter PepT1," *J. Pharma. Sci*., 87(12):1542–1546 (1988), Abstract.

Oh, D.M., et al., "Drug Transport and Targeting. Intestinal Transport," *Pharma Biotechnol*, 12:59–88 (1999), Abstract.

Balimane, P., et al., "Effect of Ionization on the Variable Uptake of Valacyclovir via the Human Intestinal Peptide Transporter (hPepT1) in CHP cells," *Biopharm Drug Dispos*, 21(5):165–174 (2000), Abstract.

Knutter, I, et al., "A Novel Inhibitor of the Mammalian Peptide Transporter PEPT1," *Biochemistry*, 40(14):4454–4458 (2001), Abstract.

Shen, H., et al., "Developmental Expression of PEPT1 and PEPT2 In Rat Small Intestine, Colon, and Kidney," *Pediatr Res*, 49(6):789–795 (2001), Abstract.

Friedrichsen, G.M., et al., "Model Prodrugs Designed for the Intestinal Peptide Transporter. A Synthetic Approach for Coupling of Hydroxy–Containing Compounds to Dipeptides," *Eur J Pharm Sci*, 14(1):13–19 (2001, Abstract.

Han H., et al., "5'–Amino Acid Esters of Antiviral Nucleosides, Acyclovir, and AZT and Absorbed by the Intestinal PEPT1 Peotide Transporter," *Pharm Res*, 15(8):1154–1159 (1998), Abstract.

Blimane, P.V., et al., "Direct Evidence for Peptide Transporter (PepT1)–Mediated Uptake of a Nonpeptide Prodrug. Valacyclovir," *Biochem Biophys Res Commun*, 250(2):246–251 (1998), Abstract.

Han, H.K., et al., "Cellular Uptake Mechanism of Amino Acid Ester prodrugs in Caco–2hPEPT1 Cells Overexpressing a Human Peptide Transporter," *Pharm Res*, 15(9):1382–1386 (1998), Abstract.

Shiraga, T., et al., "Cellular and Molecular Mechanisms of Dietary Regulation on Rat Intestinal H+/Peptide Transporter PepT1," *Gastroenterology*, 116(2):354–362 (1999), Abstract.

Guo, A., et al., "Interactions of a Nonpeptidic Drug, Valacyclovir, with the Human Intestinal Peptide Transporter (hPEPT1) Expressed in a Mammalian Cell Line," *Pharmacol Exp Ther*, 289(1):448–454 (1999), Abstract.

Amidon, G.L., et al., "5'–Amino Acid Esters of Antiviral Nucleosides, Acyclovir, and AZT are Absorbed by the Intestinal PEPT1 Peptide Transporter," *Pharm Res*, 16(2):175 (1999), Abstract.

Leibach, F.H, et al., "Peptide Transporters in the Intestine and the Kidney," *Annu Rev Nutri*, 16:99–119 (1996), Abstract.

Herrera–Ruiz, D., et al., "Spatial Expression Patterns of Peptide Transporters in the Human and Rat Gastrointestinal Tracts, Caco–2 in vitro Cell Culture Model, and Multiple Human Tissues," *AAPS PharmSci*, 3(1):E9 (2001), Abstract.

Toth, Istvan, "A Novel Chemical Approach to Drug Delivery: Lipidic Amino Acid Conjugates," *Journal of Drug Targeting*, 2:217–239 (1994).

Negishi, Naoki, et al., "Coupling of Naltrexone to Biodegradable Poly (α–Amino Acids)," *Pharmaceutical Research*, 4(4):305–310 (1987).

Zunino, Franco, et al., "Anti–Tumor Activity of Daunorubicin Linked to Poly–L–Aspartic Acid," *International Journal of Cancer*, 30:465–470 (1982).

Schmidt, Brigitte F., et al., "Peptide–Linked 1,3–Dialkyl–3–acyltriazenes: Gastrin Receptor Directed Antineoplastic Alkylating Agents," *Journal of Medicinal Chemistry*, 37(22):3812–3817 (1994).

Nishida, Koyo, et al., "Pharmacokinetic Analysis of in Vivo Metabolism of Amino Acid or Dipeptide Conjugates of Salicylic Acid in Rabbit Intestinal Microorganisms," *Pharmaceutical Research*, 11(1):160–164 (1994).

Kawai, Tohru, et al., "Direct Polymerization of N–Carboxy Anhydride of L–Glutamic Acid," *Makromol. Chem.*, 182:2127–2137 (1981).

Okada, Masahiko, "Synthesis of Glycopeptide–Conjugates via Ring–Opening Polymerization ofSugar–Substituted α–Amino Acid N–Carboxyanhydrides (GlycoNCAs)," *Proc, Japan Acad*., 73:205–209, (1997).

Kovacs, J., et al., "Glutamic and Aspartic Anhydrides. Rearrangement of N–Carboxyglutamic 1,5–Anhydride to the Leuchs' Anhydride and Conversion of the Latter to Pyroglutamic Acid," 85:1839–1844.

International Search Report for PCT/US00/05693 dated Jul. 20, 2000.

PHARMACEUTICAL COMPOSITION CONTAINING AN ACTIVE AGENT IN AN AMINO ACID COPOLYMER STRUCTURE

CROSS REFERENCE OF RELATED APPLICATION

This application is a continuation-in-part application of U.S. application Ser. No. 09/959,396 filed Oct. 24, 2001, now abandoned, which was the National Stage of International Application No. PCT/US00/05693, filed Mar. 6, 2000, which was published in English which claimed priority to provisional application 60/123,146 filed on Mar. 5, 1999; and a continuation-in-part of U.S. application Ser. No. 09/411,238 filed on Oct. 4, 1999, now abandoned, which was a continuation of U.S. application Ser. No. 09/265,415 filed on Mar. 10, 1999, now abandoned.

BACKGROUND OF THE INVENTION (i) Field of the Invention

The present invention is directed to the preparation of synthetic amino acid polymers and, more particularly, is directed to the use of these polymers to protect chemical compounds, especially drug substances, from degradation, and to release the compounds under specific conditions.

(ii) Description of Related Art

Under physiological conditions, proteins (polymer chains of peptide-linked amino acids) normally do not exist as extended linear polymer chains. A combination of molecular forces, including hydrogen bonding, hydrophilic and hydrophobic interactions, promote thermodynamically more stable secondary structures that can be highly organized (helices, beta pleated sheets, etc.). These structures can then combine to form higher order structures with critical biological functions. Natural proteins are peptide-linked polymers containing 20 different amino acids, each with a different side-chain. The details of the folding into higher order structures are dependent on the type, frequency and primary sequence of the amino acids in the protein. Since each position in the polymer chain can be occupied by 20 different amino acids, the thermodynamic rules that describe the details of protein folding are complex. For example, we are currently unable to design a synthetic protein with a substrate-specific enzymatic site that is predicted by the primary amino acid sequence. More complete discussions of the structure and function of proteins are found in Dickerson et al. "The Structure and Action of Proteins" Harper and Row, New York, 1970 and Lehninger "Biochemistry" Worth, New York, 1970, pp. 109–146.

However, some basic rules of protein folding have been discovered. In general, the side chains of the 20 L-amino acids commonly found in natural proteins can be placed in two categories, hydrophobic/non-polar and hydrophilic/polar, each playing separate roles in protein conformation. In the standard "oil drop" model for protein folding, the amino acids with more hydrophobic side chains (Val, Leu, Phe, Met, Ile) are sequestered to the inside of the protein structure, away from the aqueous environment. Frequently, these hydrophobic side chains form "pockets" that bind molecules of biological significance. On the other hand, hydrophilic amino acids (e.g. Lys, Arg, Asp, Glu) are most frequently distributed on the outer surface of natural proteins, providing overall protein solubility and establishing a superstructure for the internalized hydrophobic domains.

A highly preferred conformation found in many natural proteins is the 3.6$_{13}$ alpha-helix. This right-handed helix contains 3.6 amino acids per turn and is stabilized by hydrogen bonding (about 3 kcal/mol) involving the amide hydrogen and a carbonyl oxygen, separated by 13 atoms along the backbone of the polymer chain. Since the amino acid side chains in the alpha-helix point away from and perpendicular to the helix axis, any of the amino acids (except Pro) can participate in the helix. Other structures can also appear in higher order protein conformations, including the $3_{10}$ helix, and the important left-handed, three residue helix found in collagen and pleated sheets.

Other amino acids can also be used with predictable results in the preparation of synthetic proteins. Tyrosine (Tyr) is frequently found internalized, with its 4-hydroxy hydrogen, hydrogen-bonded to another amino acid or potential ligand/enzyme substrate. Thus, Tyr can be utilized to produce hydrophobic pockets with a potential for hydrogen bonding. Proline (Pro) has been found to be sufficient, but not always necessary, for a sharp turn in the peptide chain, allowing for cooperative interactions of different sections of the same polymer. At higher polymer concentrations, Pro can also disrupt helical structure, producing a "less organized" protein. Cysteine can be utilized to stabilize higher order structures by linking polymer chains through high energy (about 50 kcal/mol) disulfide bonds. Some amino acids do not have distinct hydrophobic or hydrophilic character and provide a "place-keeping" function or contribute more subtle effects on the overall protein structure.

Some work on synthetic polypeptides has proceeded with the goal of producing textile products with desirable properties, but the technology has been largely too expensive to compete with natural products, and with other synthetic polymers. In the pharmaceutical industry, work on synthetic polypeptides has focused again on specific amino acid sequences having intrinsic hormonal or drug activities. A more complete discussion of the use of synthetic polymers for textiles and pharmaceuticals is provided by Block in "Polymer Monographs" Gordon and Breach, Vol. 9, 1983. A historical perspective is provided by Watson "Molecular Biology of the Cell" W.A. Benjamin, Inc., New York, 1970.

Thus, it should be apparent that to date there has been in the art only a limited ability to synthesize proteins with a view to achieving a final product having a particular selected property.

SUMMARY OF THE INVENTION

It has surprisingly been found, according to the present invention, that block polymers comprised of a limited subset of amino acids, exhibit intrinsic conformational structures that can be predicted, based on an analysis of statistical distributions and ratios of the amino acids in the polymer. Moreover, it has also been surprisingly found that these synthetic proteins have utility in protecting and releasing sensitive chemical compounds. One embodiment of this invention relates to the utilization of the ability of amino acid polymers (polypeptides) to form higher order structures. These structures can bind to and protect chemical entities (e.g. drugs) from chemical and enzymatic degradation and provide a mechanism for controlled release of such entities. Synthetic polypeptides are described that are composed of carefully selected combinations and ratios of amino acids, including a hydrophilic/polar component (like Glu or Lys), a hydrophobic component (like Tyr, Phe or Benzyl Glu), and are designed to promote the formation of internalized domains, to accommodate chemical entities like drugs.

In another embodiment, the invention relates to a method of protecting a chemical compound from degradation comprising manipulating the higher order structure of a synthetic protein and combining said chemical compound with the protein. An example of such a composition may comprise combining the chemical compound with a synthetic protein which may be a homo-polymer, containing for example Glu or Lys, or may be a co-polymer with an amino acid having hydrophobic character, contributes a hydrogen bonding capacity, or stabilizes higher order structures.

In another embodiment, the invention relates to cell culture media comprising a synthetic polypeptide containing Gln that is co-polymerized with an amino acid, like Glu. The polymer provides a chemically stable nutritional source of Gln in the culture. A related embodiment utilizes a Gln containing synthetic protein as a. nutritional source of Gln in humans.

In another embodiment, the invention relates to a pharmaceutical composition comprising an active ingredient that has been combined with a synthetic amino acid polymer and a pharmaceutically acceptable excipient. The synthetic protein may be a homo-polymer of Glu or Lys, for example, or may be a co-polymer containing Glu or Lys and Tyr, Phe or Benzyl Glu. In specific related embodiments, the active ingredient of such pharmaceutical compositions is L-DOPA, aspirin, hydrocortisone, or estrogen. Such a pharmaceutical compositions may be used for example in treating Parkinson's, metabolism, or menopausal associated disorders. The protein/active ingredient combination may also be combined with other pharmaceutically acceptable excipients to aid in tablet formation and properties, for example.

In another embodiment, the invention relates to a method of controlling the release of a chemical compound based on response to changes in pH. This embodiment is comprised of manipulating the higher order structure of a synthetic protein by choice of amino acid composition and combining said chemical compound with the protein.

In another embodiment, the invention relates to the release of chemical compounds by regulating the rate of proteolytic digestion through the manipulation of higher order structures of a synthetic protein by choice of amino acid composition, and combining said chemical compounds with the protein.

In yet another embodiment, the invention relates to a method of controlling the release of a chemical compound comprising manipulating the higher order structure of a synthetic protein and combining said chemical compound with the protein.

In another embodiment, the invention relates to the release of chemical compounds by regulating thermal diffusion of said compounds from a synthetic protein. Regulation of diffusion rate occurs by manipulating the higher order structure of the synthetic protein, by choice of amino acid composition, and combining said chemical with the protein.

In another embodiment, the invention relates to a method of protecting a chemical compound from degradation comprising combining the chemical compound with an amino acid or carbohydrate polymer. The amino acid may be, for instance, a glutamic acid polymer or a glutamic acid/tyrosine copolymer.

Other embodiments, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The present invention relates to the manipulation of protein conformation in the protection and release of chemical compounds. That is, the present invention is based on the formation of higher-order structures that proteins assume under various salt, solvent and pH condition so as to protect chemical compounds and/or control the release thereof in vitro or in vivo environments. Under physiologic conditions, proteins (polypeptide chains) normally do not exist as extended linear polymer chains. A combination of molecular forces, hydrogen bonding, hydrophilic and hydrophobic interactions, cause the peptide chains to fold up into structure that can be organized (helices, beta pleated sheets, etc.) or more random. The thermodynamic rules that describe the details of this folding can be complex, for example in the unique formation of a enzymatic site.

The present invention is based upon the utilization of the natural tendency of carefully designed synthetic proteins to fold up, in order to provide protection for sensitive compounds and also provide the engineered release of these compounds. These new products provide important advantages in multiple applications.

Thus, the present invention describes the use of amino acids, to produce prototype synthetic proteins that reproduce certain conformational aspects of natural proteins. Further, the present invention describes a preferred embodiment that uses and combines a limited, but preferred sub-set of seven amino acids, each with a specific function in the resulting synthetic polypeptide: Glutamic Acid (Glu), Lysine (Lys), Phenylalanine (Phe), Proline (Pro), Tryptophan (Trp), Tyrosine (Tyr) and Cysteine (Cys). Cys is used herein as the disulfide Bis-dimer (CysS-SCys), referred to as cysteine by convention. Block polymers of this amino acid subset are used to produce synthetic proteins with predictable conformations and utility. The ability of these synthetic polypeptides to organize into higher order structures, and in some embodiments, to form hydrophobic domains, are used in the present invention to protect sensitive compounds from chemical (e.g. oxidative) and enzymatic degradation and provide for the engineered release of these compounds under specific conditions.

A number of general methods could be used in the present synthesis of synthetic polypeptides, but the most suited is the Fuchs-Farthing approach. In this method, the parent amino acid is condensed with Phosgene under anhydrous conditions to form the N-chlorocarbonyl intermediate. Depending on the specific amino acid used, the R group functionality may require protection to block involvement in the reaction. The intermediate loses HCL as it cyclizes to form the N-carboxyanhydride (NCA). Currently, it is more convenient and safe to substitute triphosgene [Bis(trichloromethyl)carbonate] for neurotoxic Phosgene (gas) since triphosgene is a crystalline solid that is easily weighed and added to the NCA reaction. Thus, triphosgene is a preferred reagent for amino acid NCA formation. Additional advantages to the Fuchs-Farthing chemistry are that the NCA's are generally easy to purify in crystalline form, negligible racemization occurs at the alpha carbon and the polymerization reaction yields only the protein polymer and non-toxic carbon dioxide.

The polymerization reaction normally contains an amino acid NCA (for homopolymers) or mixture of NCA's, for the synthesis of co- or heteropolymers, together with a polymerization initiator, all dissolved in a compatible solvent system. Highly preferred for the polymerization is a non-protic organic solvent that has high solubility for the NCA and the polymer. The preferred solvents include ethyl acetate, THF, benzene, dichloromethane, DMF and dioxane. Most preferred solvents include THF dioxane and DMF. In the case of co-polymer synthesis, solubility of the polymer in the polymerization solvent is important, since early precipitates of polymer, prior to complete use of all the NCA monomers, may favor the appearance of one amino acid over another, in the first precipitates.

The initiator of the polymerization reaction can be water, a base (organic or inorganic) or a preformed amino acid polymer. In theory, the average number of amino acid residues in the final polymer product is a direct result of the molar ratio of the monomer NCA's to the initiator. Since initiation may not behave ideally, through, for example, partitioning of the initiator into non-polymerizing compartments in the reaction, care must also be taken to use an initiator that is highly soluble in the reaction solvent. Most preferably, a tertiary amine, like triethylamine or tert-butylamine is used, since primary and secondary amines may stay covalently attached to the polymer, forming stable end-labeled polymer products.

The preferred average number of residues (N) in the polymer chains is between 5 and 400. For polymers like PGlu and PLys, where helical structure may be desired, an average N between 10 and 400 is most preferred.

Another aspect of the present invention is the claimed mechanisms of protection and release of chemical compounds from synthetic protein polymers. A useful embodiment of the invention is the formulation of tablets or liquids intended for oral delivery of an active drug substance. Standard formulations of drugs may have limited shelf-life (e.g. from oxidation) or be inactivated by the acidic conditions of the stomach. In this case, a drug delivery mechanism that circumvents the stomach would be desirable. Alternatively, rapid release of a drug substance in the stomach may be preferred.

In order to address these desired applications, chemical compounds may be formulated as defined herein. "Macro-formulation": blending of a powdered chemical compound and a powdered synthetic polypeptide prior to formulation and tableting. "Microformulation: incorporation of a chemical compound into a synthetic polypeptide, for example by inclusion into hydrophobic pockets, prior to formulation and tableting. "Covalent formulation": incorporation of a chemical compound by peptide linkages into a synthetic polypeptide prior to formulation and tableting.

A focus of the present invention makes use of a dramatic effect of pH on secondary and tertiary structures of synthetic protein polymers containing an ionizable R group (e.g. Glu, Asp, Lys, Arg). At a pH around the $pK_A$, the ionizable portion makes a transition from uncharged to highly charged. As a result of all the closely spaced repulsive charges, higher order polymeric structures, like alpha helices, are rapidly converted to "random coils." Random coils are highly flexible and dynamic; this form promotes drug release and enhanced proteolytic cleavage by digestive enzymes.

For example, a drug can be blended in powder form with polyglutamic acid (PGlu) and tableted by direct compression. Stability of the drug in this "macro-formulated" tablet is achieved by internalization of the drug into the compressed, matrix, an environment that is nearly anhydrous and low in oxygen. The presence of water and oxygen is known to be detrimental to drug stability. After ingestion, the external surface of the tablet is exposed to the low pH of the stomach (about pH=1). Since the $pK_A$ of the gamma carboxyl group of Glu is 4.25, the carboxyl groups remain in the —COOH form, the tablet remains compact, digestion of the polymer is slow and release of the co-formulated drug is slow.

However, upon passing the pyloric valve, the pH of the intestinal contents increases to about 6.5 and the carboxyl groups become de-protonated and highly, charged. The closely spaced, highly charged carboxyl groups repel each other strongly enough to overcome intrachain bonds (e.g. hydrogen bonds) responsible for higher order structure of the PGlu. The drug then diffuses from the loose, random coils of the polymer. The enhanced digestability of the random coil structure also aids drug release. Through this mechanism, the drug is released preferentially in the small intestine.

Similarly, a drug intended for oral delivery is "macro-formulated" with polymeric lysine (PLys) by blending and tableting (e.g. by direct compression). In this case, the omega amino group of Lys has a $pK_A$ of about 10.0. Once entering the stomach, the omega amino group becomes fully protonated and highly charged. The closely spaced amino groups repel each other, releasing the drug substance by diffusion and enhanced digestability of the random coil structure.

A further enhancement of drug stability and controlled release properties, especially in the digestive system, can be realized by incorporation of a hydrophobic amino acid, like Phe, to form a synthetic co-polymer. In one embodiment, a synthetic co-polymer containing Glu and Phe, in a preferred ratio is, "macro-formulated" with a hydrophobic drug substance. Stability of the drug in the compressed tablet is again enhanced by sequestration from water and oxygen. Release of the drug in stomach is slow. However, once in the small intestine, the PGlu/Phe becomes less organized due to pH/charge effects and there is an initial release of drug substance accompanied by re-partitioning of the drug into hydrophobic domains in the polymer. Finally, terminal digestive proteolysis releases the entire store of drug.

Similarly, PLys/Phe can be used for release of a drug substance in the stomach, except that drug release and digestion of the polymer are enhanced in the stomach, and the drug release profile is blunted by successive re-partitioning of the drug into the hydrophobic domain of the polymer. Finally, digestive proteolysis destroys even the hydrophobic pockets, releasing all the drug.

A further enhancement of drug stability is accomplished by microformulation involving inclusion of the drug, into the internal matrix of the synthetic protein prior to tableting and oral administration. For example, a hydrophobic drug substance is combined in solution with a co-polymer of glutamic acid and phenylalanine (PGlu/Phe) at a pH that favors the random coil form of the polymer (pH>4). The solution is slowly acidified to promote the formation of higher order structures in the polymer, with attendant formation of internalized hydrophobic domains containing the "dissolved" hydrophobic drug substance. The PGlu/Phe—Drug Substance combination precipitates at lower pH; precipitation can be enhanced by the addition of an organic solvent like acetone. The vacuum or freeze dried product is especially stable since the drug substance is partitioned into anhydrous, hydrophobic domains inside the protein structure.

A similar process of drug inclusion applies to PLys/Phe except that higher order structures, like alpha helices, occur above pH 10 for this polymer. In this case, the polymer/drug combination is adjusted to pH>11 in solution and freeze dried. Again, the product is especially stable due to partitioning of the drug into hydrophobic domains inside the protein. The polymer/drug complexes can be formulated with other excipients that may facilitate tableting.

Certain drug substances, like DOPA and glutamine (Gln), are also amino acids and are therefore amenable to co-polymerization into the primary polypeptide, chain, affording drug protection as described above and an additional control of drug release, requiring proteolytic digestion. An embodiment demonstrating the advantage of this covalent formulation is the protection of Gln from degradation. Gln is an essential amino acid for most mammalian cells and is therefore an important nutritional component, for example in cell culture. However, monomeric Gln is chemically unstable, degrading to ammonia and pyrrolidonecarboxylic acid, under physiologic conditions. Gln is chemically stabilized as a co-polymer with Glu by incorporation into the structure of the polymer. As an oral nutritional supplement in humans, Gln release is regulated by normal proteolytic digestion of the polymer. Gln is released for metabolic use by cultured cells by slow extracellular hydrolysis of the synthetic protein in the culture media or by pinocytotic mechanisms in which the synthetic protein is internalized by the cultured cells and digested by lysozomes to become a metabolic source of Gln.

Other hydrophobic amino acids find special use when co-polymerized with a hydrophilic component like Gln or Lys. For example, Tyrosine (Tyr) is moderately hydrophobic and can also hydrogen bond with potential drug substances via its 4-OH group. Tryptophan (Trp) is less hydrophobic than Phe and provides internalized hydrophobic domains that permit relatively enhanced diffusion of drug substances under physiologic conditions. Trp-NCA synthesis is also facilitated since the secondary nitrogen does not need protected.

Proline (Pro) is used in the present invention to provide obligatory turns in structures like helices, providing for enhanced intrachain interactions and promoting the formation of more globular synthetic proteins, when preferred. At higher levels, Pro destabilizes higher order protein structures since it cannot participate in helical structures and can be used in a co-polymer to enhance diffusion of a drug substance from hydrophobic domains internalized in a synthetic protein. D-amino acids also inhibit formation of helical structures of L-amino acids but are less desirable due to their possible unwanted metabolic effects as an unnatural amino acid.

Cysteine is used in the present invention to stabilize higher order structures via intra- and inter-chain disulfide linkages. This is accomplished in the present invention using the bifunctional Bis-disulfide NCA, since the disulfide linkage serves as its own thiol protecting group.

An additional embodiment of the present invention is the synthesis of a synthetic protein for use in the preparation of a synthetic serum. In this capacity, a globular protein that is metabolically stable, non-immunogenic and non-allergenic is highly desired. As an artificial serum component, a heteropolymer containing Glu, Pro, Tyr, and Cys has been prepared with the desired properties.

The synthetic polypeptides in the current application are also referred to as synthetic proteins or synthetic amino acid polymers. Polypeptides of the invention have two or more amino acids linked by a peptide bond. In a preferred embodiment, polypeptides have five or more peptide linked amino acids.

In another embodiment, the present invention relates to polypeptides containing glutamine (an essential amino acid). Monomeric glutamine is an unstable amino acid that can degrade to toxic components under normal cell culture conditions. However, according to the present invention synthetically produced polypeptides containing glutamine are used in cell culture as nutritional source of stable glutamine. For example, it has been shown that co-polymerization of glutamic acid with glutamine provides a stable form of glutamine.

This stabilization results from higher order folding of the protein structure under physiologic conditions. Slow proteolytic digestion of the protein in cell culture provides a metered release of glutamine for use by the cultured cells.

In another embodiment, longer chain synthetic polypeptides (from about 5 to about 400), containing glutamic acid and/or glutamine are used in cell culture as a serum substitute. Serum derived from bovine fetuses and other animals is routinely used in cell culture. However, serum from animals is largely undefined and may contain adventitious agents like viruses and mycoplasma, that could infect the cultured cells. A synthetic serum substitute is chronically defined with no possible risk of virus or mycoplasma infection.

In another embodiment, the polypeptide is made in various lengths to provide a mechanism for sustained release which may be performed in combination with the manipulation of the higher order structure. In such an embodiment, the varying length of the polypeptide mixture containing the drug of interest will extend the release of the therapeutic unit from the polypeptide chain, thereby providing a means whereby the frequency of dosing may be reduced. The cause of this extended release is that different length polypeptides will have different rates of hydrolysis. In addition, longer polypeptides will naturally tend to take longer to digest, and thus release the drug of interest. In this way, a mixture of polypeptides of different lengths will promote release throughout an extended period of time. Alternatively, the therapeutic agent may be protected by placing it in a carbohydrate polymer chain of varying lengths, which will similarly promote extended release of the agent.

In a preferred embodiment, the drug to be protected is L-thyroxine, iodothyronine, reverse T3 (rT3) or a related compound, containing more or fewer iodine atoms. The polypeptide in such a case will contain one or more units of L-thyroxine, iodothyronine or related compounds and be of varying length. In other preferred embodiment, the polypeptide of varying lengths may include glutamine, steroids or estrogen.

In another embodiment, carefully designed protein conformations are used to protect and release chemical compounds. Certain synthetic polypeptides provide pH and thermodynamic-dependent release of sensitive chemical entities. These producers are especially effect as pH-dependent dispersants (e g, in tablet formation) that would selectively release in the stomach or in the small intestine, depending on the specifics of the polypeptide design. Prior to release, chemical entities would be stable due to inclusion in the higher order structure of the polymer and sequestration from $O_2$, moisture, and other degradants. The careful design of the polymers with hydrophobic pockets (e.g., by inclusion of hydrophobic amino acids like tyrosine) will selectively internalize other hydrophobic molecules for slow release and protection from degradation.

The enhanced shelf life and controlled release of certain drugs is advantageous to the treatment of various disorders, including Parkinson's disease, diseases of the metabolism and conditions associated with menopause.

Unless otherwise indicated, a parameter that is qualified by "about" may vary ±10% from the stated value. That is, "about 50° C." means 45–55° C. Further, unless otherwise indicated, all amino acids are in the L-form.

The entire disclosures found in U.S. application Ser. No. 09/411,238 and the U.S. application, number not yet assigned based on PCT/US00/05693, are hereby incorporated in their entirety by reference.

The present invention, thus generally described, will be understood more readily by reference to the following examples, which are provided by way of illustration and are not intended to be limiting of the present invention.

EXAMPLES

Example 1

Preparation of Polymeric Glutamic Acid (Poly Glu)

The N-Carboxyanhydride of gamma-benzyl glutamic acid (HGlu NCA) is prepared by the method of Daly and Poche (Tet. Letters, vol. 29, p. 5859, 1988), incorporated herein by reference. For polymerization, the HGlu-NCA is prepared as a 10% solution in Tetrahydrofuran (THF) and coupling is initiated by the addition of NaOMe or organic amine, like t-butylamine. When polymerization is complete (e.g., 24 hours), the benzyl polymer (Poly BGlu) is precipitated by the addition of a suitable solvent, like petroleum ether, and the product dried in vacuo. De-benzylation of the polymer with HBr follows the method of Katchalski and Sela (J. Amer. Chem. Soc., vol. 75 p. 5284, 1953), incorporated herein by reference. The final product (Poly Glu) is obtained as a white, dry powder in about 80% yield and may be further purified, for example, by acid precipitation from aqueous solution.

Example 2

Preparation of Glutamic Acid/Glutamine Co-Polymer (Poly Glu/Gln)

The PolyBGlu is treated with Hexamethyidisilazane (HMDS, CAS 999-97-3) in THF to form the de-benzylated, silazane-derivatized polymer. This polymer is converted to any desired ratios of glutamic acid and glutamine by a combination of hydrolysis (to from the glutamine amide group) and treatment with HBr (to form the glutamic acid carboxyl group). Alternatively, PolyBGlu may be partially treated with trimethylsilyliodide (TMSI), followed by HMDS and hydrolysis to get a desired combination of Glu/Gln in the polymer. Tablets suitable for oral treatment are prepared by direct compression.

Example 3

Preparation of Glutamic Acid/Tyrosine Copolymer (Poly Glu/Tyr)

PBLG is prepared as in Example 1 except that desired amounts of Tyrosine-NCA are incorporated in the polymerization. The polymer is debenzylated in HBr to form the product containing any desired ratio of Glu/Tyr, as a block polymer. Alternatively, the Tyr-NCA can be added after 2 hours (for example) of polymerization of the Glu-NCA alone, to obtain polymers enriched in Tyr in the polymer termini. Amino acids other than Tyr can be used to advantage.

Example 4

Tablet Formation Using Poly Glu

Combinations of PolyGlu and other powdered substances can be prepared by blending a desired amount of PolyGlu and the substance, followed by direct compression to form tablets, if desired. For example, 100 mg of aspirin is combined with 100 mg of PolyGlu and the combination formed into a tablet by direct compression. Additional excipients may be used to advantage, for example to aid in blending or tablet formation.

Example 5

Treatment for Inflammation

The product of Example 4 is used as an oral preparation for the treatment of inflammation.

Example 6

Hydrophobic Inclusion by Co-Precipitation with Poly Glu-Tyr

Poly Glu/Tyr as prepared in Example 3 is co-dissolved in TNT with a desired amount of Levo-Dopa (L-Dopa). With active stirring, water is slowly added to co-precipitate the polymer and the monomeric L-Dopa. The precipitate is isolated by centrifugation or filtration and the product dried, e.g., by freeze drying. The product can be formulated and compressed into tablets.

Example 7

Treatment of Parkinson's Disease

The product of Example 6 is given as an oral preparation to patients with Parkinson's disease, as an anti-Parkinson therapy.

Example 8

Poly Glu/Gln as a Nutritional Source in Cell Culture

The product of Example 2 is combined with other culture media ingredients (not glutamine) to produce a slow release source of glutamine in cell culture. For example, glutamine dependent cells are grown in serum free and glutamine free media (e.g., NCTC-109, no glutamine) using Poly Glu/Gln as the only glutamine source. Observations of long-term growth and cell morphology demonstrate that Poly Glu/Gln is a stable, slow release source of nutritional glutamine in cell culture.

Example 9

Treatment of Glutamine Deficiency

The product of Example 2 is utilized in humans and other mammals as an effective oral treatment for glutamine deficiency.

Example 10

In vitro Stability of Glutamine as a Component of Poly Glu/Gln

The product of Example 2 was tested for stability and compared to monomeric glutamine by incubation in 0.2 M phosphate buffer at pH 9.0 as described by Price and Greenstein (J. Biol. Chem. vol. 180. p. 209, 1949), incorporated herein by reference. Glutamine in the polymer was found to be stable for over 12 hours at 37° C., while monomeric glutamine showed extensive degradation to ammonia and pyrrolidonecarboxylic acid, under the same conditions.

Example 11

Use of Poly Glu/Gln as a Synthetic Serum in Cell Culture

Human amniotic cells were cultured in media containing 5 gm/liter of Poly Glu/Gln in alpha-MBM as the basal medium. Long-term observations of cell growth and cell morphology demonstrated Poly Glu/Gln to be an adequate serum substitute. Attempts to grow the same cells without serum were not successful.

Example 12

Use of Poly Glu/Gln as a Synthetic Serum Extender in Humans

Poly Glu/Gln is useful as a serum substitute and serum extender in humans and other mammals. The product is prepared as a sterile, 0.5% solution in 0.15 N NaCl and is administered parenterally (I.V.) as needed.

Example 13

Preparation of Microcrystalline L-Glutamic Acid

L-Glutamic acid (200 gm) is dissolved in 2.5 L hot water (T>95° C.). The hot solution is added slowly to 2.5 L of rapidly stirred, cold (T<10° C.) acetone to form a thick slurry. After cooling, the precipitated solid is separated by filtration, washed with 200 ml of acetone and the filter cake compressed to remove excess solvent. The white filter cake is dried in vacuo at 80° C. for 4 hours and is suitable for use in Example 14. Yield: 189 gm (94%). "Microcrystalline" means that the crystalline nature is not obvious by macroscopic inspection; i.e., the resulting L-Glutamic acid is amorphous.

Example 14

Synthesis of Glutamic N-Carboxyanhydride (Glu-NCA)

Microcrystalline, dry L-Glutamic Acid (73.6 gm, 0.5 mol) from Example 13 is suspended in 2.0 L of anhydrous THF containing triphosgene (98 gm, 1 Eq.) and heated with stirring to 50° C. for 4 hours or until the reaction is homogeneous. The reaction is then heated to a gentle reflux for about 1 hour, using a condenser protected with a drying tube. "About 1 hour" means 1 hour±20 mm. The solution is then decanted or filtered from any remaining solids and evaporated under oil vacuum using a water bath less than 40° C. until a precipitate forms or until a thick oil remains, with no additional solvent evaporation. The product is dissolved in 360 ml of dry ethyl acetate, any insoluble material (<5 gm) is filtered off, and the crude product is precipitated by the rapid addition of 360 ml of hexanes with active stirring. After 20 min., an additional 200 ml of hexanes is added to fully precipitate the crude Glu-NCA. The precipitate is collected by filtration under a dry carbon dioxide curtain, wash the filter cake with hexanes (100 ml) and compact under pressure to remove excess solvent. In order to purify the crude Glu-NCA, the hexane-damp filter cake is dissolved in a combination of 350 ml anhydrous THF and 350 ml of anhydrous ethyl acetate. Any insoluble material is filtered off and is precipitated with rapid addition of 700 ml of hexanes with stirring. Once precipitation has commenced, an additional 350 ml hexanes is added to complete the precipitation. After 30 min., the precipitate is isolated by filtration under a dry carbon dioxide curtain. The product is compacted with pressure to remove excess solvent, and it is then washed with hexanes (100 ml) and dried in vacuo (T<30° C.). The product is stable when stored under dry carbon dioxide, in the cold (temperature is less than about 10° C., where "about 10° C." means ±5° C.).

Example 15

Synthesis of Polymeric Glutamic Acid (PGlu)

The dry (Glu-NCA product (17.3 gm, 100 mmol) of Example 14 is dissolved in anhydrous THF (86 ml) and polymerization is initiated by the addition of 86 ml of anhydrous ethyl acetate containing 0.1 gm triethylamine. The reaction is warmed to reflux for 15 min. then allowed to cool and react at 25° C. for 24 hours with continuous stirring. The precipitate is isolated by filtration, washed with anhydrous diethyl ether and dried in vacuo at 60° C. for 2 hours, to yield a white powder. Yield: 10.2 gm (79%).

Example 16

Synthesis of Polymeric Lysine (PLys)

Polymeric L-Lysine is prepared as previously described (Sela et. al., Biopolymers 1, 517, 1963). The dry polymer is converted to the alpha helical form, and contaminant bromine is removed by dissolving in water as a 10% solution and titrating the pH to 12 by the addition on 1.0 N NaOH. The spontaneous precipitate is further precipitated by the addition of acetone and collected by filtration and vacuum dried to obtain a white powder. Yield: 78% from the starting polymeric Lysine. The helical form is confirmed by measuring the optical rotation $[alpha]_D$ of the pH 12 solution (minimal negative value of −40 degrees optical rotation, compared to −130 degrees optical rotation for the random coil).

Example 17

Synthesis of Glutamic Acid/Phenylalanine Co-Polymer (PGlu/Phe)

The conditions of Example 15 are repeated except that Glu-NCA (12.46 gm, 72 mmol) and Phe-NCA (5.35 gm, 128 mmol) are co-dissolved in the THF. Crude Phe-NCA is prepared by the method of Poche (Tel. Letters 29:5859–5862, 1988). However, the crude Phe-NCA is further purified prior to polymerization by dissolving 50 gm in a mixture of 100 ml of THF and 100 ml of ethyl acetate followed by precipitation with 600 ml of hexanes. The fluffy, white product is isolated by filtration, washed with hexanes and dried in vacuo to yield 36 gm (72%).

Example 18

Synthesis of Lysine/Phenylalanine Co-Polymer (PLys/Phe)

Example 16 is repeated except that Phe-NCA is also included in the polymerization for the co-polymer in a final Lys/Phe ratio of 3.6. The polymer is converted to the helical form as described in Example 16.

Example 19

Synthesis of Glutamic Acid/Glutamine Co-Polymer (PGlu/Gln)

The polymer of Example 15 is converted to the Glu/Gln co-polymer. Polymeric glutamic acid (20 gm) is suspended in 100 ml o heated to 50° C. Concentrated aqueous ammonia (30%) is added while monitoring the pH of the solution. At pH=5.0, the mixture is stirred for an additional 10 min. while making small adjustments to pH 5.0 and the solution is freeze dried to obtain 20.4 gm of a white powder. The partial ammonium salt is then heated to 80° C. in a vacuum oven for conversion to the Glu/Gln co-polymer. Yield: 18.6 gm. Elemental analysis for N shows this preparation to contain 8% Gln. Titrations to higher pH with ammonia yield higher % Gln in the final co-polymer.

Example 20

Synthesis of Glutamic Acid/Proline/Tyrosine/Tyrosine Heteropolymer (PGlu/Pro/Cys/Tyr)

Example 15 is repeated except that 4 separate amino acid NCA's: Glu-NCA 10.71 gm, 62 mmol), Pro-NCA (1.42 gm, 10 mmol), Tyr-NCA (3.54 gm, 17 mmol) and Cys-NCA (1.14 gm, 4 mmol) are dissolved in 86 ml THF prior to polymerization. Glu-NCA is used a synthesized in Example 14. Pro-NCA, Tyr-NCA and Cys-NCA are synthesized as summarized by Blacklock, Hirschmann and Veber (The Peptides 9:39–95, 1987). Cys-NCA is prepared and used as the Bis-Cysteine-NCA (NCA-Cys-S-S-Cys-NCA). Pro-NCA is prepared just prior to use but the remaining NCA's are stable when stored as described in Example 14. Yield: 12.2 gm (76%).

Example 21

Release of Tryptophan (Trp) from PGlu+Trp Blended Tablets

A uniform blend of PGlu (19.0 gm) and Trp (1.0 gm) is prepared in a ball mill and 100 mg tablets are prepared as described in Example 25. Tablets are subjected to a standard dissolution test under two pH conditions (pH 1.0 and 6.5) in order to mimic conditions in the stomach and small intestine. In the test, a tablet is placed in a jacketed (37° C.) glass beaker containing 100 ml of the test solution, and stirred at 100 RPM. Samples (0.1 ml) of the solution are taken at 30, 60 and 120 min., diluted 1/10 in water, and the OD measured at a wavelength of 280 nanometers and compared to the control samples containing 5 mg of Trp dissolved in 100 ml of solution. Release of Trp is expressed as % of Control (100%).

| Table No. | pH = 1.0 Trp Released (% Control) | | | Ph = 6.5 Trp Released (% Control) | | |
|---|---|---|---|---|---|---|
| | 30 min | 60 min | 120 min | 30 min | 60 min | 120 min |
| 1 | 0.8 | 1.1 | 0.8 | 98.2 | 98.1 | 99.0 |
| 2 | 0.8 | 0.8 | 0.7 | 97.1 | 98.0 | 98.2 |
| 3 | .07 | 1.0 | 0.9 | 97.5 | 99.1 | 98.9 |

Example 22

Release of Tryptophan (Trp) from PLys+Trp Blended Tablets

Example 21 is repeated except that tablets were formulated using the helical form of PLys from Example 16.

| Table No. | pH = 1.0 Trp Released as % of Control | | | Ph = 6.5 Trp Released as % of Control | | |
|---|---|---|---|---|---|---|
| | 30 min | 60 min | 120 min | 30 min | 60 min | 120 min |
| 1 | 102.5 | 101.4 | 98.4 | 99.1 | 98.9 | 98.9 |
| 2 | 99.1 | 100.1 | 100.1 | 99.0 | 98.6 | 98.8 |
| 3 | 99.3 | 99.2 | 99.1 | 98.9 | 99.6 | 99.3 |

Example 23

Hydrophobic Inclusion of Tryptophan in PGlu/Phe

Tryptophan is included in hydrophobic sites in PGlu/Phe from Example 17 by dissolving 10 gm of the polymer in a solution composed of 50% ethanol and 0.05 M sodium phosphate buffer at pH 7.2.

The solution is bubbled with nitrogen to remove dissolved oxygen. Tryptophan (1.0 gm) is then added and the pH slowly adjusted to 3.0 by titration with 1.0 N HCL. The precipitate formed is collected by centrifugation and washed by re-suspension in water and the product is freeze dried. Solution of the product in 0.05 M sodium phosphate and measuring the OD at 280 nanometers is used to measure the Tip included in the polymer.

Example 24

Protection of L-DOPA by Hydrophobic Inclusion in PGlu/Phe (PGlu/Phe+DOPA)

Example 23 is repeated except that L-DOPA is substituted for tryptophan. Decomposition of DOPA is measured by formation of colored quinone oxidation products, when compared to DOPA alone. DOPA loss is measured by reverse phase HPLC as previously described. Gerlach et al., *J. Chromat.*, 380:379–385, 1986.

Example 25

Tableting for Oral Dosage Forms

Oral dosage forms of drugs combined with synthetic polypeptides can be prepared by direct compression of the polypeptide drug combination. Alternatively, the synthetic polypeptide/drug combination can be combined with other excipients to enhance tablet properties, as described for 5 mg hydrocortisone in a 200 mg tablet.

| Component | mg/Tablet | % |
|---|---|---|
| 1. Lys/Phe-Hydrocortisone | 35.0 | 17.50 |
| 2. Microcrystalline Cellulose | 25.5 | 12.75 |
| 3. Lactose | 135.25 | 67.63 |
| 4. Croscarmellose | 3.40 | 1.70 |
| 5. $Mg^{2+}$ Stearate | 0.85 | 0.42 |
| Total: | 200.00 mg | 100% |

Procedure: A pre-mix of the PLys/Phe-Hydrocortisone combination and cellulose is blended to uniformity and then blended with the remaining ingredients, except stearate, until uniform. Finally, the stearate is added and blended 5 min. Tablets are formed by direct compression to a hardness of 16 kg.

Example 26

Blending and Tableting of PGlu+Aspirin

A uniform blend of equal masses of PGlu and aspirin is prepared in a shell blender and 200 mg tablets containing 100 mg aspirin each are compressed as described in Example 25 to a hardness of 7 kg.

Example 27

Blending and Tableting of Phe/Phe+Cortisol

Example 23 is repeated except that hydrocortisone (17-hydroxycorticosterone) is substituted for Trp and tableted with other exci described in Example 25. Hydrocortisone in the tablets is determined by quantitative reverse phase HPLC of solutions containing dissolved tablets as previously described. Waters Corporation, Symmetry Applications Notebook II. August, 1994, p. 19.

Example 28

Stability of Gln in PGlu/Gln Co-Polymer

Stability of Gln in the PGlu/Gln co-polymer of Example 19 is measured by the production of free ammonia in 0.2 M phosphate buffer, as described previously (Gilbert et al., J. Biol. Chem. 180:209, 1949). The Glu/Gln co-polymer yields no detectable ammonia in this assay, while the control sample, containing free Gln is almost completely de-amidated.

Example 29

Use of PGlu/Gln in Cell Culture

The co-polymer of Example 19 is dissolved as an 0.8% solution (0.8 gm/100 ml) in a standard media, devoid of monomeric glutamine (alpha-MEM, without glutamine) and combined with insulin (5 ug/ul) and transferrin (holo, 5 µg/µl). The solution is adjusted to pH 7.2 with 1.0 N NaOH and filtered through a 0.2 micron sterilization membrane. This combined media is found to support growth of cultured human amniocytes, through multiple passages, with no addition of monomeric L-glutamine.

Example 30

Treatment of Gln Deficiency in Humans with Oral Dosage of PGlu/Gln

The Glu/Gln co-polymer of Example 19 is formed into tablets by direct compression of 125 mg of the co-polymer, as described in Example 25. This oral dose will suffice as an oral preparation to deliver about 10 mg L-glutamine, in order to treat a deficiency of this essential amino acid in humans.

Example 31

PGlu/Pro/Cys/Tyr as a Synthetic Serum Component

The heteropolymer product of example 20 is dissolved in phosphate buffered saline (PBS) and adjusted to pH 7.2 with 1.0 N NaOH, prior to sterile filtration. This sterile solution is intended as a synthetic serum replacement, to supplement serum volume in humans and other mammals.

Example 32

Treatment for Inflammation

The product of Example 26 is tableted by direct compression, as in Example, 25, to contain about 50 mg of aspirin per tablet. This preparation is intended as an oral treatment for inflammation in mammals, especially humans.

Example 33

Treatment for Primary Adrenal Insufficiency

The product of Example 27 is combined with other excipients to formulate an oral dosage for the treatment of adrenal insufficiency or inflammation in mammals, especially humans.

Example 34

Treatment for Parkinson's Disease

The product of Example 27 is tableted by direct compression, as in example 25, to contain 50 mg of L-DOPA per tablet, as oral dosage form for the treatment of Parkinson's disease in humans.

We claims:

1. A pharmaceutical composition comprising:
   (i) an active agent non-covalently linked in an internalized domain or pocket of an amino acid copolymer structure wherein said amino acid copolymer structure comprises at least one hydrophilic component and at least one hydrophobic component designed to promote the formation of said internalized domain or pocket; and
   (ii) said hydrophilic component and hydrophobic component are selected to manipulate the tertiary structure of said amino acid copolymer structure to control degradation and release of said active agent;
   wherein said hydrophilic component is lysine, arginine, asparagine, cysteine, glutamic acid or combinations thereof;
   wherein said hydrophobic component is valine, tyrosine, proline, leucine, tryptophan, methionine, phenylalanine, glycine, isoleucine, benzyl glutamic acid, or combinations thereof; and
   wherein said composition is in a form suitable for oral administration.

2. The pharmaceutical composition of claim 1, wherein said amino acid copolymer structure comprises at least one D-amino acid.

3. The pharmaceutical composition of claim 1, wherein said amino acid copolymer structure has a length between 5 and 400 amino acids.

4. The pharmaceutical composition of claim 1, wherein said amino acid copolymer structure contains is a mixture of polypeptides of varying length.

5. The pharmaceutical composition of claim 1, wherein the active agent is selected from the group consisting of a nutrient, a hormone, a neurotransmitter, and a metabolic intermediate.

6. The pharmaceutical composition of claim 1, wherein said active agent is selected from L-Dopa, 3-iodo-tyrosine, 3, 5-diiodo-tyrosine, L-thyroxine, glutamine, iodothyronine, aspirin, tryptophan and hydrocortisone.

7. The pharmaceutical composition of claim 1, further comprising at least one excipient.

8. The pharmaceutical composition of claim 7, wherein said excipient is a filler, a pH buffer, an anti-oxidant, a disintegrant, a glidant, a lubricant, or a binder.

9. The pharmaceutical composition of claim 1, wherein said amino acid copolymer structure is a copolymer of glutamic and tyrosine.

10. The pharmaceutical composition of claim 1, wherein said amino acid copolymer structure is a co-polymer of lysine and phenylalanine and the active agent is hydrocortisone.

11. The pharmaceutical composition of claim 1, wherein said amino acid copolymer structure has a free energy of folding between about 3 kcal/mol and about 50 kcal/mol.

12. The pharmaceutical composition of claim 1, wherein said amino acid copolymer structure is formulated for release of a pharmaceutically effective amount of said active agent in the small intestine.

13. The pharmaceutical composition of claim 1, wherein said amino acid copolymer is formulated for release of a pharmaceutically effective amount of said active agent in the stomach.

14. The composition of claim 1, wherein said amino acid copolymer structure is selected from co-polymers of (1) glutamic acid and phenylalanine and (2) lysine and phenylalanine; and the active agent is L-DOPA.

15. The composition of claim 1, wherein said amino acid copolymer structure is selected from co-polymers of (1) glutamic acid and phenylalanine and (2) lysine and phenylalanine; and the active agent is aspirin.

16. A pharmaceutical composition comprising:
(i) an active agent non-covalently linked in an internalized domain or pocket of an amino acid copolymer structure wherein said amino acid copolymer structure consists essentially of at least one hydrophilic component and at least one hydrophobic component designed to promote the formation of said internalized domain or pocket; and
(ii) said hydrophilic component and hydrophobic component are selected to manipulate the tertiary structure of said amino acid copolymer structure to control degradation and release of said active agent;
wherein said hydrophilic component is lysine, arginine, asparagine, cysteine, glutamic acid or combinations thereof;
wherein said hydrophobic component is valine, tyrosine, proline, leucine, tryptophan, methionine, phenylalanine, glycine, isoleucine, benzyl glutamic acid, or combinations thereof; and
wherein said composition is in a form suitable for oral administration.

17. The pharmaceutical composition of claim 1, or claim 16, wherein said amino acid copolymer structure is a copolymer of lysine and phenylalanine.

18. The pharmaceutical composition of claim 1, or claim 16, wherein said amino acid copolymer structure is a copolymer of lysine and tyrosine.

19. The pharmaceutical composition of claim 16, wherein said amino acid copolymer structure is a copolymer of glutamic acid and tyrosine.

20. The pharmaceutical composition of claim 1 or claim 16, wherein said amino acid copolymer structure is a copolymer of glutamic acid and proline.

21. The pharmaceutical composition of claim 1 or claim 16, wherein said amino acid copolymer structure is a copolymer of lysine and tryptophan.

22. The pharmaceutical composition of claim 1 or claim 16, wherein said amino acid copolymer structure is a copolymer of glutainic acid and phenylalanine.

23. The pharmaceutical composition of claim 1 or claim 16, wherein said amino acid coplymer structure is a copolymer of glutamic acid, proline, and tyrosine.

24. The pharmaceutical composition of claim 1 or claim 16, wherein said amino acid copolymer structure is a copolymer of glutamic acid, proline, cysteine and tyrosine.

25. The pharmaceutical composition of claim 1 or claim 16, wherein said amino acid copolymer structure is a copolymer arginine and at least one amino acid selected from valine, tyrosine, proline, leucine, tryptophan, methionine, phenylalanine, glycine, isoleucine, and benzyl glutamic acid.

26. The pharmaceutical composition of claim 1 or claim 16, wherein said amino acid copolymer structure is a copolymer of arginine and glycine.

* * * * *